(12) United States Patent
Paananen et al.

(10) Patent No.: US 7,060,188 B2
(45) Date of Patent: Jun. 13, 2006

(54) SEPARATION SYSTEM AND PROCESS

(75) Inventors: Hannu Paananen, Kantvik (FI); Jarmo Kuisma, Lohja (FI); Heikki Heikkilä, Espoo (FI); Vili Ravanko, Clinton, IA (US); Jari Lewandowski, Siuntio (FI); Ari Kärki, Kotka, AK (US)

(73) Assignee: Finnfeeds Finland Oy, Kantvik (FI)

( * ) Notice: Subject to any disclaimer, the term of this patent is extended or adjusted under 35 U.S.C. 154(b) by 210 days.

(21) Appl. No.: 10/787,041

(22) Filed: Feb. 25, 2004

(65) Prior Publication Data

US 2004/0251204 A1    Dec. 16, 2004

Related U.S. Application Data

(60) Provisional application No. 60/449,784, filed on Feb. 25, 2003.

(51) Int. Cl.
*B01D 15/08* (2006.01)

(52) U.S. Cl. .................. 210/659; 210/198.2; 127/46.2

(58) Field of Classification Search ................ 210/635, 210/656, 659, 662, 198.2; 127/46.1, 46.2
See application file for complete search history.

(56) References Cited

U.S. PATENT DOCUMENTS

| | | | |
|---|---|---|---|
| 5,156,736 A | | 10/1992 | Schoenrock |
| 5,565,104 A | * | 10/1996 | Priegnitz .................... 210/659 |
| 5,578,216 A | * | 11/1996 | Hotier et al. ................ 210/659 |
| 5,730,877 A | * | 3/1998 | Heikkila et al. ............ 210/659 |
| 5,755,960 A | | 5/1998 | Callebert et al. |
| 5,770,088 A | | 6/1998 | Ikeda et al. |
| 6,017,448 A | * | 1/2000 | Hotier et al. ............ 210/198.2 |
| 6,471,861 B1 | * | 10/2002 | Burgard et al. ............. 210/232 |
| 2002/0011445 A1 | | 1/2002 | Lehoucq et al. |

FOREIGN PATENT DOCUMENTS

WO    WO 01/54790 A1    8/2001

OTHER PUBLICATIONS

Karl Schoenrock, "Performance Limits in Industrial Chromatographic Separation Processes*", *Zuckerind*, vol. 122, No. 1, pp. 22-27, 1997.

Sergio Giacobello, et al., "Design of a Simulated Moving Bed Unit for Sucrose-Betaine Separations", *Journal of Chromatography A*, vol. 872, pp. 23-35, ISSN 0021-9673, 2000.

Giovanni Biressi, et al., "Design and Optimisation of a Simulated Moving Bed Unit: Role of Deviations From Equilibrium Theory", *Journal of Chromatography A*, vol. 876, pp. 3-15, 2000.

* cited by examiner

*Primary Examiner*—Ernest G. Therkorn
(74) *Attorney, Agent, or Firm*—Scully, Scott, Murphy & Presser (57) ABSTRACT

The invention relates to a system and a process for fractionating a solution into two or more fractions. The system of the invention comprises at least two compartments having a diameter of at least about one meter and including a uniform packing of a polymer-based ion exchange resin with a bead size in the range of about 50 to about 250 μm. The mixing volume of the fluid fronts in the system of the invention is not more than 5% of the volume of the compartment.

40 Claims, 2 Drawing Sheets

Figure 1.

A = Pulse width
B = Mixing volume of ascending front
C = Mixing volume of descending front

Figure 2.

SEPARATION SYSTEM AND PROCESS

This application claims the benefit of Provisional application Ser. No. 60/449,784, filed Feb. 25, 2003.

FIELD OF THE INVENTION

The present invention relates to a system and a process for fractionating a solution into two or more fractions advantageously enriched with different components using resins with a small bead size. Particularly the present invention relates to a system and a process for fractionating a solution by a chromatographic simulated moving bed (SMB) process using resins with a small bead size. The system of the invention can be applied to the fractionation of solutions like molasses solutions, vinasse solutions and sulphite cooking liquors, for example. The SMB system may be continuous or sequential or comprise a combination of a continuous process and a sequential process. The system and process of the invention is especially applied to fractionations in industrial scale columns.

BACKROUND OF THE INVENTION

The efficiency of chromatographic columns can be expressed as the number of theoretical plates. The van Deemter equation gives the height equivalent of a theoretical plate (HETP), which is dependent on the bead size, the diffusion rate and the linear flow rate.

In the case of industrial chromatography, where relatively high fluid velocities are utilized, a simplified version of the van Deemter equation can be used:

$$HETP = Ad_p + Bd_p^2 u$$

Where
$d_p$ = the bead size
u = interstitial linear velocity
$A = 2 A_m/(ud_p)$
$B = 2 \in/(1-\in)(K'_i/(1+K'_i))2/(15 D_i K_i)$
$A_m$ = axial mixing coefficient
$K_i$ = partition coefficient for component i
$K'_i$ = capacity factor for component i
$\in$ = bed porosity
$D_i$ = diffusion coefficient for component in the solid phase The pressure drop can be estimated by using the Blake-Kozeny equation $$\Delta P/L = (((1-\in)^2)/\in^3)(150\mu/d_p^2)u$$

Figure 1:
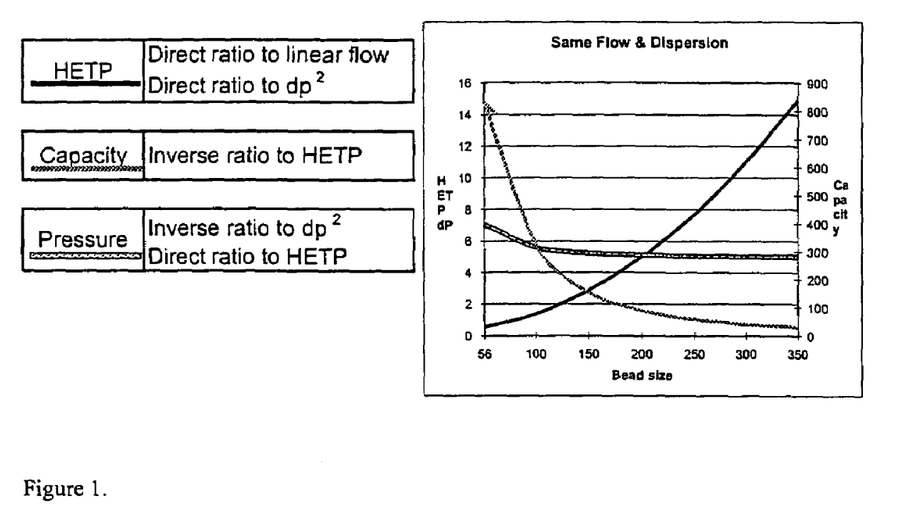
FIG. 1 shows the capacity and pressure drops versus the bead size.

Where
$\Delta P$ = pressure drop
$\in$ = bed porosity
$\mu$ = fluid viscosity
L = bed length
u = interstitial linear velocity At the same linear velocity, the same bed porosity, the same dispersion and the same number of theoretical plates, the graphs presented in FIG. 1 can be calculated, which illustrate the capacity and the pressure drops versus the bead size.

The graphs of FIG. 1 indicate clearly that much higher efficiency can be reached with a smaller bead size. Shorter resin beds can be used with a smaller bead size to give the same number of theoretical plates. The pressure drop increases with decreasing bead size, but this increase is limited by simultaneously decreasing the bed length needed for the same number of theoretical plates in a system. This approach has been used in improving the performance of analytical scale columns. Giacobello et al. have shown a similar graph in Journal of Chromatography A, 872 (2000) 23–35.

In industrial scale columns this approach has been tried but with little success.

The following problems have been noted:
- the pressure drop across the column filling material bed increases too much and limits the flow rate,
- the chromatographic peaks tail heavily causing excessive dilution and overlapping peaks
- the HETP does not decrease expectedly and the chromatographic bed has to be longer than expected,
- the achieved capacity is less than expected as a result of the decreased flow rate
- with the concentrated feed solutions and high feed loads used in industrial scale chromatography the above problems have been prohibitive.

An average bead size in the range of 300–360 µm has been used for chromatographic systems in the sweetener field. This range has offered the best compromise between the present hardware design and performance, and almost all suppliers of industrial scale chromatography use these resin sizes with a total resin bed length in the range 14–24 meters. Only one company is known to use a resin in the range of 220–240 µm and, indeed, achieves similar resolution with a resin bed of only 8 meters. However, the high pressure drops across the resin beds limit the linear flow rate in this system and the expected very high capacity has not been reached.

U.S. Pat. No. 4,673,507 (Brown) describes an apparatus and a process for ion exchange. Substantially uniform fluid flow distribution across the cross-sectional area of the bed is achieved by employing resins of a small particle size and which are maintained in an overpacked condition. Shallow beds with a high D/L ratio are shown in this patent publication.

U.S. Pat. No. 4,537,217 (Allen) describes a fluid separator apparatus and a method of fluid distribution adapted for chromatography applications. The fluid separator apparatus comprises distribution plates, which have recursive channels on one side of the plate and evenly distributed holes on the other side of the plate. However, there are several disadvantages related to this realisation. One of the embodiments is applicable as such only in a column, which is square in cross-section. For circular columns the separation apparatus comprises distribution openings, which are located within areas defined by the perimeters of concentric circles. However, the application for columns with a circular cross-section is very difficult to scale up to be used in columns with a substantially larger diameter than 0.3 m.

WO 01/54790 (Amalgamated Res. Inc.) describes a column apparatus for a fluid processing system containing a shallow bed of material between the fluid transporting fractals of a large active surface area. In said apparatus said shallow bed of material has been provided as a column having greater diameter than height. An advantage of this invention is that an over-packed bed is not required to obtain even flow distribution through the apparatus.

Biressi G. et al. (Journal of Chromatography A, 876 (2000) 3–15) indicate that the optimum column length depends on the particle size of the resin used. The smaller the particle size is the shorter the optimum column length will be.

DEFINITIONS RELATING TO THE INVENTION

In the present invention, a compartment refers to a section of the chromatographic equipment which holds a column filling material bed and which comprises a forepart for distributing the fluid to the middle part comprising the filling material bed and a rear part for collecting the fluid from this middle part.

A feed compartment refers to a section of the chromatographic equipment, which receives the feed fluid. In a sequential SMB typically one compartment receives the feed fluid. It is also possible to construct a sequential SMB so that feed enters into more than one compartment. In a continuous SMB all compartments typically receive the feed fluid once during each cycle and therefore all compartments can also be feed compartments.

A column may be composed of one or several compartments.

DESCRIPTION OF THE INVENTION

The separation system of the invention aims to achieve an order of magnitude smaller HETP using a resin bead size which is much smaller than in the presently used industrial systems. Decreasing the bead size by 50% would decrease the HETP theoretically by 75%. If the same flow rate can be maintained in such a system, the capacity would be four times higher than in the known systems. In practice such increases are not possible due to technical limitations, but it is possible to double or even triple the present capacity. However, this has not succeeded in industrial scale systems due to the problems described above.

In accordance with one aspect of the invention, the present invention relates to a simulated moving bed (SMB) system for fractionating a solution into two or more fractions, the system comprising at least two compartments having a diameter of at least about one meter and including a uniform packing of a polymer-based ion exchange resin with a bead size in the range from about 50 to about 250 µm as the column filling material, wherein the system provides a mixing volume of the fluid fronts between two adjacent compartments of not more than 5% of the volume of the compartment.

According to the present invention, the problems related to known industrial systems using a small bead size have been solved with the following parameters:

1. The smaller the bead size is, the shorter compartments can be used.

If the HETP decreases by 75%, then also the height of the compartment can be decreased by roughly the same amount (=50–75%). This minimizes the pressure drop increase caused by the smaller bead size and allows similar linear flow rates to be maintained with reasonable pressure ratings.

2. The movement of the resin in the compartment is minimized.

This can be realized in practice by packing the compartment full of resin so that during normal operation the compartment remains full and uniform.

3. The compartments are uniformly and fully packed with the filling material. This means that the resin has a uniform and narrow size distribution and the packing system enables the achievement of uniform packing.

4. When the compartments are short, it is important to minimize the mixing volume caused by the distribution and collection devices in the compartments and the intermediate piping between the compartments.

The compartments used in the system of the present invention are filled with a polymer-based ion exchange resin having a bead size in the range from about 50 to about 250 µm, preferably from about 100 to about 200 µm, more preferably from about 125 µm to about 160 µm. In one preferred embodiment of the invention the compartment is filled with a polymer-based ion exchange resin having a bead size of about 125 to about 130 µm. The resin should have a uniform size distribution. Preferably 75% and more preferably 80% of the resin beads are within ±20% range from the mean bead size.

The column filling material may be selected from cation exchange resins and anion exchange resins. The resin is selected depending on the raw material mixture to be fractionated and/or the products to be recovered. The resins and their properties are well known to those skilled in the art.

The polymer base of the resin refers to a styrene or acrylic skeleton. The acrylic skeleton is preferably derived from methyl acrylate, ethyl acrylate, buthyl acrylate, methylmethacrylate or acrylonitrile or acrylic acids or mixtures thereof. The styrene and acrylic skeleton may be crosslinked with a crosslinking agent, e.g. divinyl benzene (DVB). A suitable crosslinking degree is from about 1 to about 20%, preferably from about 3 to about 8%.

The cation exchange resin may be a strong acid cation exchange resin or a weak acid cation exchange resin. The cation exchange resin may be in a monovalent and/or divalent metal form, such as $Na^+$ and/or $K^+$ form, or $Ca^{2+}$, $Ba^{2+}$, $Mg^{2+}$ and/or $Sr^{2+}$ form. Resins in $H^+$ and $NH_4^+$ form may also useful. However, also other ionic forms may be used.

The anion exchange resin may be a strong base or a weak base anion exchange resin, having preferably an acrylic skeleton. The anion exchange resins may be in $OH^-$, $Cl^-$ or $SO_4^{2-}$-form. However, also other ionic forms may be used.

One preferred column filling material in the system of the invention is a strong acid cation exchange resin in a monovalent metal form, which is predominantly in $Na^+$ and/or $K^+$ form. Another preferred column filling material in the system of the invention is a weak acid cation exchange resin in a monovalent metal form, which is predominantly in $Na^+$ and/or $K^+$ form.

The resins may be of the macroporous type or gel-type resins. Preferably the resins are gel-type resins.

Manufacturers of resins are for example Finex, Dow, Bayer and Rohm & Haas.

Zeolites, carbonaceous pyropolymers and activated carbon bound to a polymer are also useful as column filling materials.

The compartment of the system of the present invention is typically short/shallow. The height of the compartment is preferably about 0.2 to 2.0 meters. More preferably the height of the compartment is about 0.5 to 1.5 meters. The optimum height of the compartment is related to the bead size as the following preferred embodiments show.

In one preferred embodiment of the invention, the bead size of the resin is from about 100 to about 160 µm. The optimum compartment height is between 0.5 and 1.0 meters and the ratio of the diameter to the height of the compartment is in the range of from about 6 to about 12. The total resin bed height is typically from 2 to 6 meters.

In another preferred embodiment of the invention, the bead size of the resin is from about 170 to about 250 µm. The optimum compartment height is between 1.0 and 2.0 meters and the ratio of the diameter to the height of the compartment is from about 2 to 6. The total resin bed height is typically from 6 to 15 meters.

The height of the compartment preferably corresponds to the height of the resin bed in said compartment. The volume of the compartment preferably corresponds to the volume of the packed resin bed in said compartment.

The movement of the resin in the compartment should be minimized. This is done in practice by packing the compartment full of resin so that during normal operation the compartment remains full. In accordance with the present invention, the compartment has uniform packing. Uniform packing means that the compartment is fully packed with a resin having a uniform size distribution in a way which enables the achievement of an equal/even resistance of flow across the whole cross-section area of the resin bed in the compartment. In practice, the volume of the compartment preferably corresponds to the volume of the resin bed in the compartment. Preferably, the uniform packing is maintained essentially unchanged during normal operation. The compartments are preferably designed so that the mechanical pressure caused by the resin can be tolerated.

SMB systems are normally realized with multiple compartments and/or columns in series, which form the total chromatographic bed. A typical industrial SMB system may comprise 2–20 compartments and/or columns. The optimum performance/cost ratio can normally be achieved with systems comprising 3–8 compartments and/or columns. The compartments and/or columns are filled with filling material, which does the actual chromatographic separation. Between the individual compartments and/or columns the fluid moving in the system is collected from the filling material bed in the column upstream into a pipeline with a collection device. The pipeline may contain online instruments like a density meter, conductivity meter, polarimeter, refractometer, pressure meter etc. The pipeline normally goes into a pump, which acts as a pressure booster between the compartments and/or columns. The pump discharge goes through a pipeline to the next compartment and/or column downstream. Also this pipeline may contain on-line instruments like a flow meter, pressure meter etc. A distribution device distributes the flow to the top of the resin bed in the next compartment and/or column downstream.

Each resin bed does a certain amount of separation, which is based on the separation factors between the components in the feed and the length of the bed. If the separation factor is 1, the components are not separated at all. If the separation factor differs from 1, the components will be separated, if a long enough chromatographic bed is available. If the separation factor is higher than 2 or smaller than 0.5 but different from 1, a relatively short chromatographic bed can provide good separation. In most sugar applications, the separation factors are normally from 0.5 to 0.9 or from 1.1 to 2, which means that the peaks are only separated by a relatively small amount in each individual column.

The mixing between compartments and/or columns caused by the collection device(s), distribution device(s), pipelines, on-line instrumentation, pumps etc. should always be an order of magnitude smaller than the separation effected by each resin bed. Otherwise the mixing between compartments and/or columns destroys or significantly reduces the separation, which the resin bed achieves. If each bed can separate the desired components by 20% of the bed volume and the actual mixing volume between the beds is 10% of the bed volume, this will naturally decrease the separation efficiency by roughly 50%.

It should be noted that this mixing volume is not directly related to the actual physical volumes of the pipelines, pumps, distribution and collection devices etc. The mixing volume is dependent on how well the distribution and collection devices are working. It can only be measured by suitable testing methods. A test can be done by injecting a sharp concentration gradient (concentration increases, for example, from 1 to 45 g/100 ml in a very small volume like 1 liter) into the system and by measuring to what extent this gradient becomes less sharp by the mixing caused in the pipelines, pumps, distribution and collection devices etc., which are typically between the compartments and/or columns. The mixing in the resin bed should be minimized in the test system. By measuring how many liters it takes for the concentration to increase from 1 to 45 g/100 ml at the outlet of the measured system, the mixing volume can be determined by deducting the original gradient volume from the measured volume of the output gradient.

Particularly, when the compartment and/or column is short/shallow (0.2–2.0 m), it is important to minimize the mixing volume caused by the distribution and collection device within the compartment. Similarly it is important to minimize the mixing volume in the intermediate piping between the adjacent compartments.

The mixing volume refers to the mixing of the fluid fronts in the distribution and collection devices and in the intermediate piping between the adjacent compartments. The mixing volume in the system should not exceed 5% of the volume of the compartment. Preferably it should not be more than 2%. In a compartment with a height of 1 m, the mixing volume should not exceed 5 cm and should preferably be less than 2 cm of the compartment.

The system of the present invention enables the use of compartments having a diameter of 1 meter or more.

Preferably the distribution device distributes the fluid into a compartment evenly with minimum time delay, with minimum time delay distribution and with minimum mixing of the fluid fronts.

Preferably the collection device collects the fluid from a compartment evenly with minimum time delay, with minimum time delay distribution and with minimum mixing of the fluid fronts.

The fluid is also distributed and/or collected with minimum turbulence throughout the cross-section of the compartment. The lack of time delay and minimum time delay distribution in the distributing and/or collecting of the fluid in a separation operation enhance the separation of the desired fractions. Preferably, when the distributing and/or collecting device is used in a compartment and/or a column, for example in a chromatographic column, the mixing volumes of the fluid fronts are at minimum. The small mixing volume of the fluid front enables a better utilisation of the column filling material. This means that a better separation of the desired products can be achieved with a smaller amount of column filling material.

Fluid front means the concentration gradient between different components in the moving phase, for example the concentration gradient between the feed and the eluent. Time delay in the distributing and/or collecting device is the volume of the device divided by the flow rate of the fluid. Time delay distribution is the spread of the distributing/collecting times. Minimum time delay distribution means that the fluid introduced to a compartment and/or a column is distributed from each point in the distributing device essentially at the same time or that the fluid flowing out of a compartment and/or a column is collected from each point in the collecting device essentially at the same time.

A preferred distributing and/or collecting device is described in a copending application PCT/FI03/00989, which is incorporated herein by reference.

In one embodiment of the invention, the feed compartment of the system is shorter than one or more of the other compartments of the system. The feed compartment may be shorter than all other compartments of the system. In one embodiment of the invention, the feed compartment is shorter than the next compartment of the system.

Optionally the system of the present invention comprises a feed compartment which is short/shallow compared to the total height of the chromatographic column. The height of the feed compartment is preferably equal to or less than 1/6 of the total height of the compartments of the equipment. More preferably the height of the feed compartment is equal to or less than 1/8 of the total height of the compartments of the equipment.

In the above embodiments of the invention, where the feed compartment is short/shallow, the combined mixing volume of the fluid fronts is not more than 5%, preferably not more than 2% of the volume of the shorter one of the adjacent compartments.

Use of the shallow feed compartment improves further the performance figures of the SMB equipment and the separation process essentially. The so-called viscous fingering phenomenon is substantially minimized and the tailing effect of the chromatograms is then correspondingly decreased. The tailing effect of the chromatograms is a real problem with industrial chromatographic applications where the linear flows and loads of dry substances are heavy. In addition, the shallow feed compartment design minimizes resin movement. The resin movement in a column is random and as being irregular and turbulent, blends the frontiers and decreases the separation results of an SMB process.

The height of the resin bed in the feed compartment preferably corresponds to the height of said compartment. The volume of the resin bed in the compartment preferably corresponds to the volume of said compartment.

In another aspect of the invention, the invention relates to a process for fractionating a solution into two or more fractions with an SMB system, wherein the system comprises at least two compartments having a diameter of at least about one meter and including a uniform packing of a polymer-based ion exchange resin with a bead size in the range of about 50 to about 250 μm and wherein the mixing volume of the fluid fronts in the fractionation is not more than 5% of the volume of the compartment.

The preferred embodiments of the process of the invention are the same as described above for the system of the invention.

The system and process of the present invention can be applied to the fractionation of solutions such as molasse solutions, vinasse solutions and sulphite cooking liquors using a SMB method. The SMB method may be continuous or sequential or comprise a combination of a continuous process and a sequential process.

Preferably the SMB method is a sequential SMB method.

Preferably the SMB method utilized is a two-profile method or repeated looping method. These methods are disclosed in detail in U.S. Pat. No. 6,224,776 or U.S. patent application Ser. No. 20010009236 and U.S. patent application Ser. No. 20030006191, respectively. Said U.S. Patent and patent applications are incorporated herein by reference.

The system and process of the invention works well with high superficial velocities (volumetric flow rate/column cross sectional area), typically velocities higher than 1 meter/hour.

The system and process of the invention are especially useful for concentrated feed solutions having a feed load more than 10 kg dry substance per one cubic meter of the column volume per one cycle.

The system and process of the invention are particularly well suitable for separating substances that are difficult to separate from mixtures containing them. Such feed mixtures typically include the following: sulphite cooking liquors, molasses, especially B-molasses and/or C-molasses, vinasse, fructose and/or glucose syrups, beet-derived juices, invert sugar mixtures, starch hydrolysates, wood hydrolysates, milk whey solutions and other lactose-containing solutions, lactulose-containing solutions, maltose-containing solutions, maltitol-containing solutions, solutions containing amino acids, fermentation broths containing various organic acids, such as citric acid, gluconic acid, bagasse hydrolysates, solutions containing rhamnose, arabinose, mannose, raffinose, inositol, mannitol, sorbitol, xylitol, erythritol, glutamic acid, glycerol, tagatose, isomaltulose, trehalose, ribose, 6-O-α-D-glucopyranosido-D-sorbitol (1,6-GPS) and 1-O-α-D-glucopyranosido-D-mannitol (1,1-GPM) etc. Preferably, the solution to be fractionated is a molasses solution, a vinasse solution or a sulphite cooking liquor. The molasses solution preferably comprises beet and/or cane molasses. As used herein, the term "sulphite cooking liquor" means a liquor employed in the cooking of sulphite cellulose or a part thereof, a liquor ensuing from the cooking or a part thereof, a liquor used in the sulphite cooking or a part thereof or a liquor removed from the sulphite cooking during the cooking or a part thereof.

The products that are recovered using the system of the invention include glucose, fructose, sucrose, betaine, rhamnose, arabinose, mannose, raffinose, lactose, lactulose, maltose, maltitol, inositol, mannitol, glycerol, xylitol, xylose, sorbitol, erythritol, ribose, 6-O-α-D-glucopyranosido-D-sorbitol (1,6-GPS) and 1-O-α-D-glucopyranosido-D-mannitol (1,1-GPM), organic acids, and/or especially amino acids, such as glutamic acid.

The selectivity of a chromatographic separation is illustrated by a separation factor α ($\alpha=k_1/k_2$, where $k_1$ is the retention factor for compound 1 and $k_2$ is the retention factor for compound 2). The system of the invention is particularly well suitable for separating substances having a separation factor from about 0.5 to about 2.

The eluent used in the method of the invention described above is preferably water, but even solutions of salts and water are useful. Furthermore, alcohols, such as ethanol, and mixtures of water and alcohol, such as a mixture of water and ethanol are useful eluents.

The temperature of the chromatographic fractionation depends on the selected resin, for instance. The temperature in the chromatographic fractionation is typically in the range of 50 to 100° C., preferably 55 to 90° C. It is known that a higher separation temperature decreases the viscosity and improves the separation performance.

In addition to chromatography, the method of the invention can also be applied to ion exchange or adsorption systems.

The invention will be further clarified by the following examples, which describe the performed tests but should not be considered as limiting the applicability of the invention. Examples 1, 2 and 3 describe pilot scale systems using columns with a diameter less than 1.0 m. Example 4 illustrates the measurement of the mixing volume in a very short resin bed having a diameter of 1.0 m. Example 4 indicates that the mixing volume constraints of the present invention can be fulfilled with columns having a large diameter of 1 meter and over.

EXAMPLE 1

SMB Chromatography Test with a 350 µM Bead Size Cation Exchange Resin

The test equipment included six columns connected in series, a feed pump, recycling pumps, an eluent water pump as well as inlet and product valves for the various process streams. The equipment included flow control units to control the feed flow, the eluent flow and the circulation step flow. Conductivity meters were used in each column to measure the conductivity of the out-coming flow and a density meter was used in last column to measure the density of the out-coming flow. The height of each column was 4 m and each column had a diameter of 0.111 m. The columns were packed with a 350 µm bead size strong acid gel type cation exchange resin (DOW 99K/350) in $Na^+$-form. 98% of the resin beads were measured to be in ±20% range from the mean bead size.

The compartment(s)/column(s) were fully and uniformly packed with the resin using a 8% salt solution to shrink the resin during the packing operation so that the resin bed effectively fills the whole compartment. The salt concentration was chosen so that during the normal operation the salt concentration in any compartment of the system never exceeds the salt concentration during the packing of that compartment. This ensures that the compartments stay fully packed during the operation and the resin movement within a compartment is effectively minimized.

The feed material was beet molasses. The molasses was diluted to 60 weight-% and carbonated with sodium carbonate (1.5% on DS basis, temperature 60° C., 3 h reaction time). The carbonated solution was then filtered with a Seitz pressure filter using Kenite 300 as a filtering aid (pre-coat 1 kg/m$^2$, body-feed 0.5% on DS basis). The feed concentration was adjusted to 69.6 g/100 ml. The composition of the feed is set forth in the table below, whereby the percentages are given on the dry substance weight basis.

TABLE 1

| Composition of feed | |
| --- | --- |
| Concentration, g/100 ml | 69.6 |
| pH, - | 9.3 |
| Sucrose, % on DS | 56.5 |
| Betaine, % on DS | 6.9 |
| Others, % on DS | 36.6 |

The fractionation was performed by way of a 9-step sequence of a two-profile SMB process as set forth below (the process is disclosed in detail in U.S. Pat. No. 6,224,776). The feed and the eluent were used at a temperature of 85° C. and water was used as the eluent.

Step 1: 2.0 l of feed solution was pumped into the first column at a flow rate of 45 l/h and a recycle fraction was collected from column 6.

Step 2: 9.8 l of feed solution was pumped into the first column at a flow rate of 42 l/h and a residual fraction was collected from the same column. Simultaneously 10.1 l of water was pumped into column 2 at a flow rate of 43 l/h and a residual fraction was collected from column 4. Also simultaneously water was pumped into column 5 at a flow rate of 72 l/h and firstly 4.4 l of recycle fraction and then 12.2 l of sucrose-containing fraction were collected from column 6.

Step 3: 1.8 l of feed solution was pumped into the first column at a flow rate of 45 l/h and a sucrose-containing fraction was collected from column 6.

Step 4: 7.5 l was circulated in the column set loop (the separation profile circulation was continued), formed with all columns, at a flow rate of 48 l/h.

Step 5: 1.0 l of water was pumped into the first column at a flow rate of 50 l/h and a betaine-containing fraction was collected from column 6.

Step 6: 10.2 l of water was pumped into the first column at a flow rate of 62 l/h and a residual fraction was collected from column 2. Simultaneously 10.2 l of water was pumped into column 3 at a flow rate of 63 l/h and a residual fraction was collected from column 5. Also simultaneously 3.7 l of water were pumped into column 6 at a flow rate of 23 l/h and a betaine-containing fraction was collected from the same column.

Step 7: 10.3 l of water were pumped into the first column at a flow rate of 53 l/h and a betaine-containing fraction was collected from column 6.

Step 8: 10.1 l of water were pumped into the first column at a flow rate of 59 l/h and a residual fraction was collected from column 3. Simultaneously water was pumped into column 4 at a flow rate of 58 l/h and firstly 3.0 l of betaine-containing fraction and then 6.8 l of residual fraction were collected from column 6.

Step 9: 8.2 l was circulated in the column set loop, formed with all columns, at a flow rate of 50 l/h.

During the SMB chromatography test steps 1, 2, 3, 4, 5, 6, 7, 8 and 9 were repeated at least 9 times. After equilibration of the system, the following fractions were drawn from the system: a residue fraction from all columns, sucrose-containing fractions from column 6, recycle fractions from column 6 and betaine-containing fractions from column 6. The results including HPLC analyses for the combined fractions are set forth in Table 2 below.

TABLE 2

| Fractions | Sucrose | Betaine | Recycle | Residual |
| --- | --- | --- | --- | --- |
| PH, - | 10.3 | 9.6 | 9.7 | 7.3 |
| Volume, l | 14.0 | 18.0 | 6.4 | 57.2 |
| Concentration, g/100 ml | 31.4 | 4.1 | 21.2 | 5.5 |
| Sucrose, % on DS | 94.2 | 0.7 | 61.2 | 10.8 |
| Betaine, % on DS | 0.0 | 83.2 | 0.0 | 0.4 |
| Others, % on DS | 5.8 | 16.1 | 38.8 | 88.8 |

The overall yield calculated from the product fractions is 92.3% for sucrose and 98.0% for betaine. The total length of the separation cycle was 72 min and the separation capacity based on product fractions was 29.7 kg dry substance/hour/m$^3$ resin.

The mixing volume was estimated to be 1.7% of the resin bed volume.

EXAMPLE 2

SMB Chromatogrpahy Test with a 220 µM Bead Size Cation Exchange Resin

The test equipment included six columns connected in series, a feed pump, recycling pumps, an eluent water pump as well as inlet and product valves for the various process streams. The equipment included flow control units to control the feed flow, the eluent flow and the circulation step flow. Conductivity meters were used in each column to measure the conductivity of the out-coming flow and a density meter was used in the last column to measure the density of the out-coming flow. The height of columns 1, 3, 4 and 6 was 1.5 m and the height of columns 2 and 5 was 1.8 m. Each column had a diameter of 0.111 m. The columns were packed uniformly with a 220 μm bead size strong acid gel type cation exchange resin (Mitsubishi UBK 530) in Na$^+$-form. 95% of the resin beads were measured to be in ±20% range from the mean bead size.

The compartment(s)/column(s) were fully and uniformly packed with the resin using a 8% salt solution to shrink the resin during the packing operation so that the resin bed effectively fills the whole compartment. The salt concentration was chosen so that during the normal operation the salt concentration in any compartment of the system never exceeds the salt concentration during the packing of that compartment. This ensures that the compartments stay fully packed during the operation and the resin movement within a compartment is effectively minimized.

The feed material was beet molasses. The molasses was diluted to 60 weight-% and carbonated with sodium carbonate (1.5% on DS basis, temperature 60° C., 3 h reaction time). The carbonated solution was then filtered with a Seitz pressure filter using Kenite 300 as a filtering aid (pre-coat 1 kg/m$^2$, body-feed 0.5% on DS basis). The feed concentration was adjusted to 69.6 g/l 100 ml. The composition of the feed is set forth in Table 3, whereby the percentages are given on a dry substance weight basis.

TABLE 3

| Composition of feed | |
| --- | --- |
| Concentration, g/100 ml | 69.6 |
| pH, - | 9.3 |
| Sucrose, % on DS | 6.3 |
| Betaine, % on DS | 5.6 |
| Others, % on DS | 38.1 |

The fractionation was performed by way of a 8-step sequence of a two-profile SMB process as set forth below (the process is disclosed in detail in U.S. Pat. No. 6,224,776) as set forth below. The feed and the eluent were used at a temperature of 85° C. and water was used as an eluent.

Step 1: 1.2 l of feed solution was pumped into the first column at a flow rate of 40 l/h and a recycle fraction was collected from column 6.

Step 2: 3.1 l of feed solution was pumped into the first column at a flow rate of 34 l/h and a residual fraction was collected from the same column. Simultaneously 3.4 l of water was pumped into column 2 at a flow rate of 37 l/h and a residual fraction was collected from column 4. Also simultaneously water was pumped into column 5 at a flow rate of 76 l/h and firstly 1.4 l of recycle fraction and then 5.6 l of sucrose-containing fraction were collected from column 6.

Step 3: 0.4 l of feed solution was pumped into the first column at a flow rate of 40 l/h and a sucrose-containing fraction was collected from column 6.

Step 4: 4.3 l was circulated in the column set loop (separation profile circulation was continued), formed with all columns, at a flow rate of 40 l/h.

Step 5: 4.0 l of water was pumped into the first column at a flow rate of 55 l/h and a residual fraction was collected from column 2. Simultaneously 4.0 l of water was pumped into column 3 at a flow rate of 55 l/h and a residual fraction was collected from column 5. Also simultaneously 2.5 l of water were pumped into column 6 at a flow rate of 32 l/h and a betaine-containing fraction was collected from the same column.

Step 6: 3.9 l of water were pumped into the first column at a flow rate of 50 l/h and a betaine-containing fraction was collected from column 6.

Step 7: 3.4 l of water were pumped into the first column at a flow rate of 55 l/h and residual fraction was collected from column 3. Simultaneously water was pumped into column 4 at a flow rate of 62 l/h and firstly 1.0 l of betaine-containing fraction and then 2.7 l of residual fraction were collected from column 6.

Step 8: 2.8 l was circulated in the column set loop, formed with all columns, at a flow rate of 50 l/h.

During the SMB chromatography test steps 1, 2, 3, 4, 5, 6, 7 and 8 were repeated at least 9 times. After equilibration of the system, the following fractions were drawn from the system: a residue fraction from all columns, sucrose-containing fractions from column 6, recycle fractions from column 6 and betaine-containing fractions from column 6. The results including HPLC analyses for the combined fractions are set forth in Table 4 below.

TABLE 4

| Fractions | Sucrose | Betaine | Recycle | Residual |
| --- | --- | --- | --- | --- |
| PH, - | 10.3 | 9.5 | 9.6 | 7.8 |
| Volume, l | 6.0 | 7.4 | 2.6 | 20.6 |
| Concentration, g/100 ml | 28.0 | 3.0 | 17.7 | 5.1 |
| Sucrose, % on DS | 93.0 | 2.8 | 50.8 | 8.2 |
| Betaine, % on DS | 0.0 | 737 | 0.1 | 1.6 |
| Others, % on DS | 7.0 | 23.5 | 49.1 | 90.2 |

The overall yield calculated from the product fractions is 94.4% for sucrose and 90.7% for betaine. The total length of the separation cycle was 33 min and the separation capacity based on product fractions was 57.8 kg dry substance/hour/m$^3$ resin.

The mixing volume was estimated to be 2.2% of the resin bed volume.

EXAMPLE 3

SMB Chromatography Test with a 127 μM Bead Size Cation Exchange Resin

The test equipment included six columns connected in series, a feed pump, recycling pumps, an eluent water pump as well as inlet and product valves for the various process streams. The equipment included flow control units to control the feed flow, the eluent flow and the circulation step flow. Conductivity meters were used in each column to measure the conductivity from the out-coming flow and a density meter was used in last column to measure the density of the out-coming flow. The height of each column was 0.5 m and each column had a diameter of 0.111 m. The columns were packed with a 127 μm bead size strong acid gel type cation exchange resin (Finex CS13GC) in Na$^+$-form. 80% of the resin beads were measured to be in ±20% range from the mean bead size.

The compartment(s)/column(s) were fully and uniformly packed with the resin using several 20% salt solution pulses to shrink the resin during the packing operation so that the resin bed effectively filled the whole compartment. The salt concentration was chosen so that during the normal operation the salt concentration in any compartment of the system never exceeds the salt concentration during the packing of that compartment. This ensures that the compartments stay fully packed during the operation and the resin movement within a compartment is effectively minimized.

The feed material was beet molasses. The molasses was diluted to 60 weight-% and carbonated with sodium carbonate (1.5% on DS basis, temperature 60° C., 3 h reaction time). The carbonated solution was then filtered with a Seitz pressure filter using Kenite 300 as a filtering aid (pre-coat 1 kg/m$^2$, body-feed 0.5% on DS basis). The feed concentration was adjusted to 55.3 g/100 ml. The composition of the feed is set forth in table 5 below, whereby the percentages are given on a dry substance weight basis.

TABLE 5

| Composition of feed | |
|---|---|
| Concentration, g/100 ml | 55.3 |
| pH, - | 9.5 |
| Sucrose, % on DS | 54.8 |
| Betaine, % on DS | 5.4 |
| Others, % on DS | 39.8 |

The fractionation was performed by way of a 9-step sequence of a two-profile SMB process as set forth below (the process is disclosed in detail in U.S. Pat. No. 6,224,776). The feed and the eluent were used at a temperature of 85° C. and water was used as an eluent.

Step 1: 0.5 l of feed solution was pumped into the first column at a flow rate of 45 l/h and a recycle fraction was collected from column 6.

Step 2: 0.7 l of feed solution was pumped into the first column at a flow rate of 30 l/h and a residual fraction was collected from the same column. Simultaneously 1.0 l of water was pumped into column 2 at a flow rate of 60 l/h and a residual fraction was collected from column 4. Also simultaneously water was pumped into column 5 at a flow rate of 80 l/h and firstly 0.5 l of recycle fraction and then 0.9 l of sucrose-containing fraction were collected from the column 6.

Step 3: 0.4 l of feed solution was pumped into the first column at a flow rate of 40 l/h and a sucrose-containing fraction was collected from column 6.

Step 4: 1.1 l was circulated in the column set loop (separation profile circulation was continued), formed with all columns, at a flow rate of 40 l/h.

Step 5: 0.3 l of water was pumped into column 6 at a flow rate of 65 l/h and a residual fraction was collected from the column 2.

Step 6: 0.6 l of water was pumped into the first column at a flow rate of 55 l/h and a residual fraction was collected from column 2. Simultaneously 0.9 l of water was pumped into column 3 at a flow rate of 52 l/h and a residual fraction was collected from column 5. Also simultaneously 0.7 l of water were pumped into column 6 at a flow rate of 70 l/h and a betaine-containing fraction was collected from the same column.

Step 7: 1.5 l of water were pumped into the first column at a flow rate of 55 l/h and a betaine-containing fraction was collected from the column 6.

Step 8: 1.0 l of water were pumped into the first column at a flow rate of 57 l/h and a residual fraction was collected from column 3. Simultaneously water was pumped into column 4 at a flow rate of 71 l/h and firstly 0.5 l of betaine-containing fraction and then 0.7 l of residual fraction were collected from the column 6.

Step 9: 1.2 l was circulated in the column set loop, formed with all columns, at a flow rate of 45 l/h.

During the SMB chromatography test, steps 1, 2, 3, 4, 5, 6, 7, 8 and 9 were repeated at least 9 times. After equilibration of the system, the following fractions were drawn from the system: a residue fraction from all columns, sucrose-containing fractions from column 6, recycle fractions from column 6 and betaine-containing fractions from column 6. The results including HPLC analyses for the combined fractions are set forth in table 6 below.

TABLE 6

| Fractions | Sucrose | Betaine | Recycle | Residual |
|---|---|---|---|---|
| pH, - | 10.4 | 9.1 | 9.8 | 7.5 |
| Volume, l | 1.3 | 2.7 | 1.0 | 5.2 |
| Concentration, g/100 ml | 29.6 | 2.5 | 19.9 | 4.9 |
| Sucrose, % on DS | 92.7 | 7.1 | 57.5 | 10.8 |
| Betaine, % on DS | 0.3 | 67.6 | 0.2 | 0.5 |
| Others, % on DS | 7.0 | 25.3 | 42.3 | 88.7 |

The overall yield calculated from the product fractions is 91.7% for sucrose and 94.9% for betaine. The total length of the separation cycle was 11.5 min and the separation capacity based on product fractions was 127.2 kg dry substance/hour/m$^3$ resin.

The mixing volume was estimated to be 4.0% of the resin bed volume.

EXAMPLE 4

Measuring the Mixing Volume in a Compartment with a Very Short Resin Bed and a Large Diameter The previous examples show that a significant improvement in the separation capacity can be achieved by using filling materials with significantly smaller bead size than in the current industrial practice. These SMB tests were done with pilot scale columns. In order to show that the same kind of improvement can be achieved with industrial columns having a large diameter, the following test unit was constructed for measuring the mixing volume in a large diameter column. The test equipment included a column, a feed tank and an eluent tank, a feed solution pump and an eluent water pump and inlet valves for the both feed streams. The equipment included also a mass flow meter (Micro Motion) to measure the flow and the density of the out-coming flow, a conductivity meter to measure the conductivity of the out-coming flow and a flow control unit to control the feed and eluent flows to the column.

The distribution and collection devices were built as presented in the co-pending patent application PCT/FI03/00989.

The height of the resin bed was 2 cm corresponding to the height of the column compartment. The diameter of the column was 1.0 m. The very short resin bed was selected in order to minimize the mixing caused by the resin bed and to indicate clearly how much mixing the combination of feed pumps, pipelines, distribution device, collection device and on-line instrumentation associated with resin bed can cause. The column was packed full with a 350 μm bead size strong acid gel type cation exchange resin (DOW 99K/350) in Na$^+$-form. The resin was packed in the column in a salt solution to ensure that the compartment was fully filled with the resin.

As the feed, 45 weight-% sucrose-salt solution was used (80% sucrose and 20% NaCl on the dry substance weight basis). The feed and the eluent water were used at a temperature of 85° C. and before test the column and the resin were heated with a constant eluent flow. 40 liters of the feed solution was pumped into the column with a flow rate of 40 l/min as the first step. 100 liters of eluent water was pumped to the column with a flow rate of 40 l/min as the second step and feed solution was eluted from the column.

Figure 2:
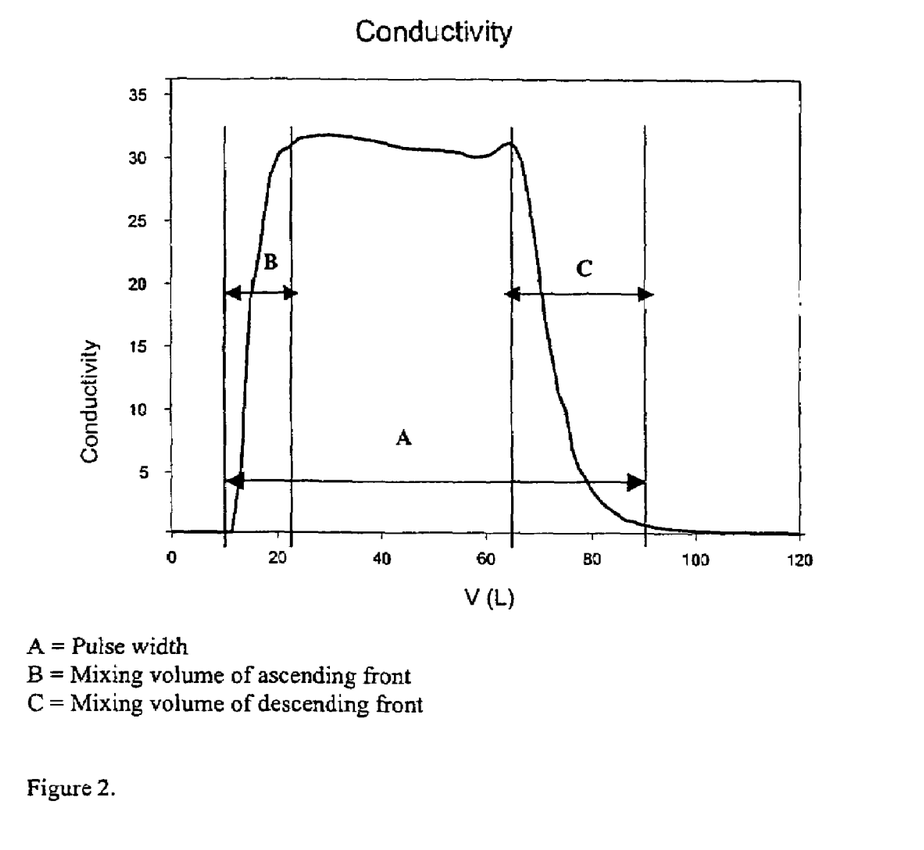
FIG. 2 shows the conductivity profile at the outlet of the column in Example 4.

FIG. 2 shows the conductivity profile at the outlet of the column. From this profile we can see that the output pulse width is about 80 liters. The input pulse was 40 liters wide and, therefore, the output has become 40 liters wider. The mixing in the pipelines, distribution device, 2 cm resin bed, collection device, pipelines and on-line instrumentation causes this pulse widening. The pulse has two concentration fronts, which are mixed: the ascending front and the descending front. Therefore the mixing volume can be determined for both the ascending and the descending fronts. The mixing volume for the ascending front is about 10–12 liters and about 22 liters for the descending front determined from the conductivity profile in FIG. 2. These volumes include the mixing and chromatographic separation caused by the resin bed (2 cm height=16 liters' bed volume). This mixing volume should be deducted from the above figures to get the actual mixing volume caused by the pipelines, instruments, distribution and collection devices. However, there is no way to measure this mixing volume reliably so we have to rely on the measured mixing volumes and note that the true mixing volumes must be smaller than the measured. The ascending front has a mixing volume of less than 10–12 liters, which in a 1 m diameter column means less than 1.2–1.5 cm of the empty column height. The descending front has a mixing volume of less than 22 liters, which in a 1 m diameter column means less than 2,8 cm of the empty column height. With the 5% mixing volume limit, this would mean that the minimum height compartment would be 2,8 cm/0.05=56 cm high. This shows clearly that the invention can be realized in large diameter columns using these types of distribution and collection devices.

The invention claimed is:

1. An SMB system for fractionating a solution into two or more fractions, the system comprising at least two compartments having a diameter of at least about one meter and including a uniform packing of a polymer-based ion exchange resin with a bead size in the range from about 50 to about 250 μm, and wherein the system provides a mixing volume of the fluid fronts of not more than 5% of the volume of the compartment.

2. The system according to claim 1, wherein the bead size of the resin is from about 100 to about 200 μm.

3. The system according to claim 1, wherein the bead size of the resin is from about 125 to about 160 μm.

4. The system according to claim 1, wherein 75% of the beads are within +/−20% range from the mean bead size.

5. The system according to claim 1, wherein the volume of the packed resin bed corresponds to the volume of the compartment.

6. The system according to claim 1, wherein the resin is packed uniformly in the compartments so that the resin movement in the compartments is effectively minimized.

7. The system according to claim 1, wherein the resin is a strong cation exchange resin.

8. The system according to claim 7, wherein the resin is in a monovalent metal form.

9. The system according to claim 8, wherein the monovalent metal is $Na^+$.

10. The system according to claim 8, wherein the monovalent metal is $K^+$.

11. The system according to claim 8, wherein the monovalent metal is a mixture of $Na^+$ and $K^+$.

12. The system according to claim 7, wherein the resin is in a divalent metal form.

13. The system according to claim 12, wherein the divalent metal is $Ca^{++}$.

14. The system according to claim 12, wherein the divalent metal is $Mg^{++}$.

15. The system according to claim 1, wherein the resin is a weak cation exchange resin.

16. The system according to claim 1, wherein the resin is a strong anion exchange resin.

17. The system according to claim 1, wherein the resin is a weak anion exchange resin.

18. The system according to claim 1, wherein the resin is in a gel form.

19. The system according to claim 1, wherein the height of the compartment is from about 0.2 to about 2.0 m.

20. The system according to claim 19, wherein the height of the compartment is from about 0.5 to about 1.5 m.

21. The system according to claim 20, wherein the total height of the compartments is in the range of from about 2 to 6 m.

22. The system according to claim 1, wherein the bead size of the resin is from about 100 to 160 μm and the height of the compartment is in the range of from about 0.5 to 1.0 m.

23. The system according to claim 22, wherein the ratio of the diameter to the height of the compartment is in the range of from about 6 to 12.

24. The system according to claim 1, wherein the bead size of the resin is from about 170 to 250 μm and the height of the compartment is from about 1.0 to 2.0 m.

25. The system according to claim 24, wherein the ratio of the diameter to the height of the compartment is in the range of from about 2 to 6.

26. The system according to claim 24, wherein the total height of the compartments is in the range of from about 6 to 15 m.

27. The system according to claim 1, wherein the mixing volume of the fluid fronts is not more than 2% of the volume of the compartment.

28. The system according to claim 1, wherein the feed compartment is shorter than one or more of the other compartments of the system.

29. The system according to claim 28, wherein the feed compartment is shorter than the other compartments of the system.

30. The system according to claim 28, wherein the feed compartment is shorter than the next compartment of the system.

31. The system according to claim 28, wherein the height of the feed compartment is equal to or less than ⅙ of the total height of the compartments of the system.

32. The system according to claim 31, wherein the height of the feed compartment is equal to or less than ⅛ of the total height of the compartments of the system.

33. The system according to claim 28, wherein the mixing volume of the fluid fronts is not more than 5% of the volume of the shorter one of the adjacent compartments.

34. The system according to claim 33, wherein the mixing volume of the fluid fronts is not more than 2% of the volume of the shorter one of the adjacent compartments.

35. The system according to claim 1, wherein the separation factor is 0.5–2.0 but differs from 1.

36. The system according to claim 1, wherein the SMB system is a sequential SMB system.

37. The system according to claim 1, wherein the solution to be fractionated is selected from sulphite cooking liquors, molasses, especially B-molasses and/or C-molasses, vinasse, fructose and/or glucose syrups, beet-derived juices, invert sugar mixtures, starch hydrolysates, wood hydrolysates, milk whey solutions and other lactose-containing solutions, lactulose-containing solutions, maltose-containing solutions, maltitol-containing solutions or solutions containing amino acids.

38. The system according to claim 37, wherein the solution to be fractionated is selected from a molasses solution, a vinasse solution and a sulphite cooking liquor.

39. The system according to claim 1, wherein the product to be recovered is one or more of the following: glucose, fructose, sucrose, betaine, rhamnose, arabinose, mannose, raffinose, lactose, lactulose, maltose, maltitol, inositol, mannitol, glycerol, xylitol, xylose, sorbitol, erythritol, ribose, 6-O-α-D-glucopyranosido-D-sorbitol (1,6-GPS) and 1-O-α-D-glucopyranosido-D-mannitol (1,1-GPM), organic acids or amino acid, such as glutamic acid.

40. A process for fractionating a solution into two or more fractions with an SMB system, wherein the system comprises at least two compartments having a diameter of at least about one meter and including a uniform packing of a polymer-based ion exchange resin with a bead size in the range of about 50 to about 250 μm and wherein the mixing volume of the fluid fronts in the fractionation is not more than 5% of the volume of the compartment.

* * * * *